United States Patent [19]

Hara et al.

[11] Patent Number: 4,717,664

[45] Date of Patent: Jan. 5, 1988

[54] METHOD FOR PRODUCING SECONDARY METABOLITES OF PLANTS

[75] Inventors: Yasuhiro Hara; Chuzo Suga, both of Ootake, Japan

[73] Assignee: Mitsui Petrochemical Industries, Ltd., Tokyo, Japan

[21] Appl. No.: 766,672

[22] Filed: Aug. 16, 1985

Related U.S. Application Data

[63] Continuation of Ser. No. 405,104, Aug. 4, 1982, abandoned.

[30] Foreign Application Priority Data

Aug. 11, 1981 [JP] Japan ................................ 56-124765
Aug. 11, 1981 [JP] Japan ................................ 56-124766
Aug. 11, 1981 [JP] Japan ................................ 56-124767
Aug. 11, 1981 [JP] Japan ................................ 56-124768
Aug. 11, 1981 [JP] Japan ................................ 56-124769
Aug. 11, 1981 [JP] Japan ................................ 56-124764

[51] Int. Cl.$^4$ .......................... C12P 7/66; C12P 1/00; C12P 17/16; C12P 17/18; C12P 17/10; C12P 17/12; C12P 7/00; C12N 5/00; C12N 5/02

[52] U.S. Cl. ..................................... 435/133; 435/41; 435/118; 435/119; 435/121; 435/122; 435/132; 435/240.54; 435/240.48

[58] Field of Search ................. 435/240, 241, 41, 132, 435/133, 118, 119, 121, 122; 47/59, 62

[56] References Cited

FOREIGN PATENT DOCUMENTS

| | | |
|---|---|---|
| 0007244 | 1/1980 | European Pat. Off. . |
| 0022434 | 1/1981 | European Pat. Off. . |
| 0050562 | 4/1982 | European Pat. Off. . |
| 3029991 | 3/1978 | Japan . |
| 0039779 | 3/1982 | Japan . |
| 0039778 | 3/1982 | Japan . |
| 7039779 | 3/1982 | Japan . |
| 0063081 | 4/1982 | Japan . |
| 0063082 | 4/1982 | Japan . |
| 2025959 | 1/1980 | United Kingdom . |

OTHER PUBLICATIONS

Tabata: in Plant Tissue Culture and its Bio-Technological Application, Barz et al. (ed.), Springer-Verlag, 1977, pp. 3-16.
Zenk et al.: in Plant Tissue Culture and its Bio-Technological Application, Barz et al. (ed.), Springer-Verlag, 1977, pp. 27-43.
Yamada et al.: Chem. Abstr. 95:30273v (1981) of Phytochemistry 20: 545 (1981).
Yadrov et al.: Chem. Abstr. 89:145697e (1978) of Restit. Res. 14: 408 (1978).
*Manual of the Vascular Flora of the Carolinas,* Radford et al., 1968, The University of North Carolina Press, Chapel Hill, N.C., pp. 925 and 935.
Phytochemistry, vol. 13, p. 927 (1974) Abstract only, Tabata et al.
Phytochemistry, vol. 16, p. 1183 (1977) Abstract only, Mizukami et al.
Phytochemistry, vol. 17, p. 95—(1978) Abstract only, Mizukami et al.
Pharmacological Journal, vol. 95, p. 1376, Tabata et al. (1975) Abstract only.
Chem. Abst., vol. 93, Oct. 1980, p. 414, Item 146587p., Kato et al.
Kato, J. Ferment. Technol. (1980), vol. 58(4), pp. 373-382.

*Primary Examiner*—James Martinell
*Attorney, Agent, or Firm*—Cushman, Darby & Cushman

[57] ABSTRACT

This invention provides for a method for producing secondary metabolites of higher plants, such as *Lithospermum erythrorhizon, Coptis japonica,* and *Nicotinia tabacum,* by suspension cultures of a mass of undifferentiated cells (callus). The cultures are carried out in at least two stages in liquid media. The first stage culturing is carried out in a liquid medium conventionally used for the tissue culture of plants, which contains indispensably inorganic substances and carbon sources and, additionally, phytohormones, vitamins and/or amino acids. While, the second stage culturing is carried out in another liquid medium, of which the concentration of at least one of the constituents is substantially varied, namely decreased or increased, from the first stage liquid medium. According to such two stage liquid medium cultures, the productivity of the second metabolites, such as shikonin, berberine and nicotine, are significantly increased, even though the rate of cell growth in the second stage is relatively low.

9 Claims, No Drawings

METHOD FOR PRODUCING SECONDARY METABOLITES OF PLANTS

This is a continuation of application Ser. No. 405,104, filed Aug. 4, 1982, which was abandoned upon the filing hereof.

The present invention relates to a method for producing secondary metabolites of plants with high efficiency by using a mass of undifferentiated cells (callus). More particularly, this invention relates to a method for producing secondary metabolites with high efficiency by culturing the cell group preliminarily proliferated in a liquid medium suited to the growth of the cell, again in a modified liquid medium suited to the production of secondary metabolites.

To date, several attempts have been made to obtain secondary metabolites by culture of a mass of undifferentiated cells of a plant (callus). For example, the roots of *Lithospermum erythrorhizon* Sieb. et Zucc. (Boraginaceae) contain naphthoquinone derivatives such as shikonin (R=—OH) as represented in the formula below,

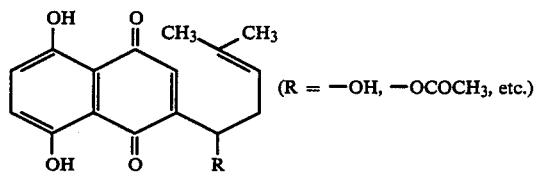

(R = —OH, —OCOCH$_3$, etc.)

and have been conventionally used as a material of the Chinese herb medicines being called "Shikon" (literally meaning "purple root"). That is, the ointments obtained by extracting shikonin and other substances from such plant roots with sesame or other oil are called "Shi Un Ko" and known to possess anti-inflammatory activity and stimulate the formation of granulation tissue, among other medical actions. Thus, they are used as topical medications for dermal diseases, wounds, burns, hemorrhoids, etc.

However, the amount of the effective substances such as shikonin which can be extracted from the plant roots is very slight. The cultivation of *L. erythrorhizon* takes a long time and the harvesting depends on the natural environments and weather conditions. Thus, the stable supply of shikonin is difficult.

Incidentally, experiences of proliferation of *L. erythrorhizon* plants by using the cell culture method have been reported by M. Tabata, H, Mizukami, and others in "Phytochemistry" Vol. 13, page 927, "Pharmacological Journal" Vol. 95, page 1376, "Phytochemistry" Vol. 16, page 1183, and Vol. 17, page 95. These methods are quite advantageous because *L. erythrorhizon* plants may be proliferated steadily, regardless of the season and weather.

However, these conventional methods employ agar solid media and require complicated operations in the proliferation process, and are not suited to the mass production of cell group. Yet, the productivity of the secondary metabolites, such as naththoquinone derivatives, is insufficient.

On such background, the present inventors have searched for a method using liquid medium which is suited to mass production of cell group, and first tried to use a liquid medium obtained by removing the agar constituent from the solid medium (Linsmaier-Skoog medium) which has previously been used by Tabata et al, in the cell culture of *L. erythrorhizon*. As a result, though the cell group proliferated, the production of shikonin and other naphthoquinone derivatives, which are the secondary metabolites, was scarce and the productivity was unstable.

After further study, the inventors have found that the amount of the secondary metabolites obtained from cells is significantly increased when the cells are cultured stepwise in two kinds of liquid media having specific relation each other, and have finally reached the present invention.

Thus, the present invention relates to a method for producing secondary metabolites of plants which is characterized by that the cells of a plant proliferated in a liquid medium (first stage) containing inorganic substances and carbon sources as he essential constituents and additionally containing at least one of phytohormones vitamins and amino acids, are again suspension cultured in a modified liquid medium (second stage) substantially changed in the concentration of at least one of the substances used in the first liquid medium.

The liquid medium employable in the first stage of the present invention (referred to as "liquid medium (A)") may be one of those conventionally used for the plant cultures, which contains indispensably inorganic substances and carbon sources and, additionally, at least one of phytohormones, vitamins and amino acids.

Among the inorganic substances, there may be mentioned nitrogen, phosphorus, potassium, calcium, magnesium, sulfur, iron, manganese, zinc, boron, copper, molybdenum, chlorine, sodium, iodine, cobalt, etc. Typically, there may be illustrated potassium nitrate, sodium nitrate, calcium nitrate, potassium dihydrogen phosphate, disodium hydrogen phosphate, potassium chloride, calcium chloride, magnesium sulfate, sodium sulfate, iron(II) sulfate, iron(III) sulfate, manganese sulfate, zinc sulfate, boric acid, copper sulfate, sodium molybdate, molybdenum trioxide, potassium iodide, cobalt chloride, and the like.

As the carbon sources, carbohydrates such as sucrose, their various derivatives, organic acids such as fatty acids, primary alcohols such as ethanol, and others, may be illustrated.

The phytohormones or plant hormones may include, for example, auxins such as indoleacetic acid (IAA) napthaleneacetic acid (NAA), p-chlorphenoxyisobutyric acid, 2,4-dichlorophenoxyacetic acid (2,4-D) and the like; cytokinins such as kinetin, 6-benzyladenine (BA), 6-(3-methyl-2-butenylamino)purine (2ip), zeatin, dihydrozeatin and the like.

The vitamins may include biotin, thiamine (vitamin B$_1$), pyridoxine (vitamin B$_6$), pantothenic acid, ascorbic acid (vitamin C), inositol, nicotinic acid, and the like.

The amino acids may include glycine, alanine, glutamine, cysteine, and the like.

The concentrations of each substance in the liquid medium (A) may be varied in a wide range. Usually, the medium is prepared by adding the inorganic substances within a range of about 0.1 $\mu$M to 200 mM, for example, 40 to 130 mM of N, 0.8 to 2.4 mM of P, 10 to 45 mM of K, 0.015 to 0.15 $\mu$M of Cu, 30 to 300 $\mu$M of Mn, 1 to 15 $\mu$M of I, 0.05 to 0.5 $\mu$M of MoO$_4$, and 0.5 to 3 mM of SO$_4^-$; carbon sources about 1 g/liter to 30 g/liter; phytohormones about 0.01 $\mu$M to 10 $\mu$M, for example, 0.01 to 10 $\mu$M of cytokinin; vitamins about 1 mg/liter to about 500 mg/liter; and amino acids about 0.1 mg/liter to about 100 mg/liter.

The liquid medium (A) is preferably one of those suited to growth or proliferation of cells. Practical examples may include Linsmaier-Skoog's medium, Gamborg et al.'s B-5 medium, and their modified media.

The plant cells used in the present invention are callus or a mass of the undifferentiated cells, prepared by taking a tissue sample from a plant body, such as roots, growing poing, leaves, stems and seeds, and sterilizing it, adding it to a solid medium, and profiferating a part of the tissue to a mass of undifferentiated cells or callus.

The species of plants applied are not particularly limited, but may include, among others, Juglandaceae plants such as chestnut, Boraginaceae plants such as *L. erythrorhizon*, Pyrolaceae plants such as *Pyrola incarnata* and *Chimaphila japonica*, Plumbaginaceae plants such as Plumbago, Lythraceae plants such as *Lawsonia inermis*, Ranunculaceae plants such as *Coptis japonica*, and Solanaceae plants such as *Nicotinia tabacum*.

In case of Boraginaceae plants, for example, tissue pieces of a plant body are sterilized, and placed on a Linsmaier-Skoog solid medium and cultured for about 7 to 30 days at 10° to 35° C. to convert a part of the tissue pieces to callus. When the thus obtained callus is cultured for generations, the growth rate is gradually accelerated, and stabilized calluses are obtained. These calluses are applied to the liquid medium (A) of the first stage culturing of the present invention.

The initial concentration of the callus in the liquid medium (A) may be varied in a wide range. Usually, it is preferable to add about 1 to 200 g (as of fresh weight) of callus in 1 liter of the liquid medium.

In the first stage, the liquid medium (A) is preferably that suited to the growth or the proliferation of callus. More preferably, the callus is accelerated in its growth rate by successive culturing in the liquid medium (A) beforehand.

In case of Boraginaceae plants, the secondary metabolites composed of naphthoquinone derivatives may be produced in some extent even in the first stage, but the amount is slight. The condition suited to the proliferation of callus may not necessarily be good for production of the secondary metabolites.

In the present invention, it is particularly important to encourage at the first stage the proliferation of cells, and when the cells having such history is used, the production of the secondary metabolites such as naphthoquinone derivatives can be further increased in the second stage in the modified liquid medium (referred to as "liquid medium (B)").

In case of *L. erythrorhizon*, it is advantageous to merely proliferate callus in the first stage, usually 4 to 21 days, without encouraging production of the naphthoquinones, and then to proceed to the second stage, usually 7 to 12 days.

The cells cultured in the liquid medium (A) in the first stage are separated from the medium, and are added into a modified liquid medium (B) in the second stage, and the cell cultures are continued.

In the composition of the modified liquid medium (B), the concentration of at least one of the substances in the liquid medium (A) should be substantially modified, that is, increased or decreased.

In the liquid medium (B), of which the concentration of at least one of the constituents is substantially varied from that in the liquid medium (a), such constituent may be preferably selected from inorganic substances, phytohormones, vitamins and amino acids.

Among those, of which the concentration of the constituent is lowered, primarily effective are inorganic nitrogen, inorganic phosphorus, and inorganic potassium compounds, typically, ammonium ion, nitrate ion, phosphate ion and potassium ion. While, secondarily effective are calcium ion, iron ion, manganese ion, cobalt ion, iodine ion, molybdate ion, sodium ion, chlorine ion and the like inorganic substances, as well as cytokinins, vitamins and amino acids.

The concentrations of each constituents in the liquid medium (B) may be decreased to not more than 1/5 in case of inorganic nitrogen, inorganic phosphorus and inorganic potassium compounds; not more than 1/10 in case of manganese ion, iodine ion, and molybdate ion; not more than 1/10 in case of vitamins; and not more than 1/100 in case of amino acids and cytokinins, as per the concentrations in the liquid medium (A).

On the other side, copper ion and sulfate ion are those which are preferably increased in the concentrations in the liquid medium (B). The concentration of copper ion may be increased to not less than 3 times, and the concentration of sulfate ion, to not less than 10 times, as per those in the liquid medium (A).

Referring now to the culturing in the modified liquid medium in the second stage of the present invention, which is prepared by substantially varying the concentration of at least one of the constituents of the liquid medium (A), the embodiments are explained by classifying them into seven types for the sake of convenience.

One of the preferable embodiments of the present invention is a method of lowering the concentration of at least one inorganic nitrogen, inorganic phosphorus, and inorganic potassium compounds at the second stage. That is, the present invention is to provide for a method for producing secondary metabolites of plants, which is characterized by culturing the cells of a plant obtained by culturing (in the first stage) in a liquid medium for plant tissue culture, containing inorganic nitrogen in an amount of 40 to 130 mM, inorganic phosphorus in an amount of 0.8 to 2.4 mM and inorganic potassium compounds in an amount of 10 to 45 mM, again (in the the second stage) in a modified liquid medium wherein the concentration of at least one of the inorganic nitrogen, the inorganic phosphorus and the inorganic potassium compounds, in the first liquid medium is lowered to 1/5 or less.

The second preferred embodiment is a method to increase copper ion concentration in the second stage. That is, the present invention is to provide for a method of producing secondry metabolites of plants which is characterized by that the concentration of the copper ion used in the medium of the first stage ranges from 0.01 to 0.15 $\mu$M and that in the second stage is not less than three times that of the first stage. In this invention, so far as the concentration of copper ion in the liquid medium (B) is not less than three times that of the first stage, namely not less than 0.45 $\mu$M, more particularly, adjusted within a range of 0.2 $\mu$M to 25 $\mu$M, the other elements in the medium may be varied in a wide range, so that the media used conventionally in cell cultures of plants may be used by modifying them variably. When the copper ion concentration is less than three times, the production amount of naphthoquinone derivatives decreases, and if the concentration is over 25 $\mu$M, no significant changes are observed, but the productivity decreases slightly.

The third preferred embodiment is a method of lowering the concentration of at least one of manganese ion, iodine ion and molybdate ion in the second stage. That is, the present invention is to provide for a method of producing secondary metabolites of plants which is characterized by that the manganese ion concentration of the medium used in the first stage is within a range of 30 to 300 $\mu$M, iodine ion concentration within 1 to 15 $\mu$M and molybdate ion concentration within 0.05 to 0.5 $\mu$M, and the concentration of at least one constituent selected from manganese ion, iodine ion and molybdate ion of the medium in the second stage is 1/10 or less of the ion concentration in the first stage. In this invention, it is preferable to control the concentrations of at least two elements thereof, and it is the most preferable to control the concentrations of all of the three constituents. More particularly, the concentrations of the three constituents is preferably controlled in the values as low as possible within the conditions specified for the second stage above, and it is ultimately preferable to use a liquid medium not containing any of such elements at all. As a results, the production of naphthoquinone derivatives in the cells may be further increased.

The fourth preferred embodiment is a method of lowering the total concentration of the vitamins used in the second stage. That is, the present invention is to provide for a method of producing secondary metabolites of plants which is characterized by that the total concentration of the vitamins in the medium used in the first stage is 1 to 500 mg/liter and that in the second stage is 1/10 or less of that in the first stage.

The fifth preferred embodiment is a method of lowering the total concentration of the amino acids used in the second stage. That is, the present invention is to provide for a method of producing secondary metabolites of plants which is characterized by that the total concentration of amino acids in the medium used in the first stage is 0.1 to 100 mg/liter and that in the second stage is 1/100 or less of that in the first stage.

In the fourth and fifth embodiments of the present invention, it is preferable to control, as specified hereinabove, the concentration of at least one constituent selected from vitamins: (a) inositol, (b) thiamine, (c) pyridoxine, (d) nicotinic acid, and (e) ascorbic acid, and the concentration of at least one constituent selected from amino acids; (f) glycine, (g) L-cystine, and (h) L-glutamine. It is more preferable to control the concentrations of at least two constituents in each category, and it is the most preferable to control the concentrations of all of constituents from (a) to (h).

More particularly, the concentrations of the constituents (a) to (h) may preferably be controlled in the values as low as possible within the conditions specified for the second stage above, and it is ultimately preferable to use a liquid medium containing no such constituents at all. As a result, the production of naphthoquinone derivatives in the cells may be further increased.

The sixth preferred embodiment is a method of lowering the total concentration of cytokinins used in the second stage. That is, the present invention is to provide for a method for producing secondary metabolites of plants which is characterized by that the total concentration of cytokinins in the medium used in the first stage is 0.01 $\mu$M to 10 $\mu$M and that in the second stage is 1/100 or less of that in the first stage. The cytokinins used in the present invention may include, besides kinetin, 6-benzyladenine, 6-(3-methyl-2-butenylamino)purine (2ip), zeatin, dihydrozeatin and the like.

The seventh, the final, preferred embodiment is a method of increasing the concentration of sulfate ion used in the second stage. That is, the present invention is to provide for a method for producing secondary metabolites of plants which is characterized by that the concentration of sulfate ion in the medium used in the first stage is 0.5 to 3 mM and that in the second stage is 10 times or more of that in the first stage.

In the seven embodiments as mentioned above, the concentrations of other constituents than those of which concentration is substantially varied in the second stage may be varied in a wide range. Ordinarily, the inorganic components are adjusted within a range of about 0.1 $\mu$M to 200 mM, carbon sources within about 1 g/liter to 30 g/liter, phytohormones within about 0.01 $\mu$M to 30 $\mu$M, vitamins within about 1 mg/liter to 500 mg/liter, and amino acids within about 0.1 mg/liter to 100 mg/liter.

Besides, in the present invention, it is also possible to further increase the naphthoquinone derivatives by compositely adjusting the constituents in the medium of the second stage by suitably combining any of the seven types of embodiments. Particularly favarable is a combination of all of the seven types.

Generally, the rate of cell growth in the liquid medium (B) in the second stage is relatively lower than that in the liquid medium (A) in the first stage, but the productivity of the secondary metabolites such as naphthoquinone derivatives significantly increases to the contrary.

The initial concentration of cells in the liquid medium (B) may be varied in a wide range as in the case of liquid medium (A). The period of time for the second stage cultures is 10 to 28 days, preferably 14 to 21 days.

The present invention brings about favorable effects in particular when Boraginaceae plants are used to obtain shikonin and other naphthoquinone derivatives as the secondary metabolites.

However, the applications of the invention are not limited to L. erythrorhizon alone, but the advantages of the present invention may be equally enjoyed, for example, when obtaining berberine by applying the method to Coptis japonica or obtaining nicotine by applying the method to Nicotinia tabacum. Specifically in these cases, the effects of the present invention will be magnified by the increase of copper ion concentration as disclosed in the second type of embodiment.

In case of Boraginaceae plants, cell cultured do not necessarily require light, and a dark place is rather preferable for the production of the secondary metabolites such as shikonin. The culture temperature may be within a range of about 10° C. to about 35° C., preferably within 23° C. to 28° C. approximately. At a temperature lower than 10° C., the cell proliferation rate is low, and when the temperature exceeds 35° C., the proliferation rate also reduces.

Naphthoquinone derivatives may be separated from the cells and the liquid medium (B) by, for example, the conventional extraction method to obtain natural "Shikon" products.

According to the present invention, secondary metabolites may be efficiently produced from cells of higher plants. Besides, since liquid media are used, upgrading of the scale of continuous operation would be easy, and the secondary metabolites can be produced in large quantities by simple operations.

The present invention is not limited to the culture in two stages by using two kinds of liquid media, but it is possible to culture the cells in three stages or more by using three or more kinds of liquid media, so far as the conditions of the present invention are satisfied.

This invention is further described below by referring to the working examples, which are, however, for the purpose of exemplification and not for the limitation of the present invention.

EXAMPLES 1 TO 3, AND COMPARATIVE EXAMPLE 1

(Culture in the first stage)

Thirty mililiters of a modified Linsmaier-Skoog liquid medium ($A_1$), having a composition as shown in Table 1 (containing 1 μM of indoleacetic acid, 10 μM of kinetin, and 30 g/liter of sucrose) was put into a 100 ml Erlenmeyer flask, and sterilized for 10 minutes at 120° C.

After being cooled, 0.5 g of fresh callus of *L. erythrorhizon* (obtained by culture on the agar medium) was added to the above medium ($A_1$), and was cultured at 25° C. for a period of 14 days on a rotary shaker at agitation diameter of 25 mm and speed of 100 rpm.

Using 0.5 g of the cells obtained by above mentioned culture, the same operation was repeated (usually twice). As a result, the growth of cells in the modified liquid medium ($A_2$) was stabilized.

(Culture in the second stage)

The second stage was conducted by using the above medium ($A_1$) or a medium ($B_1$, $B_2$ or $B_3$) shown in Table 1 which was prepared by increasing or decreasing the concentration of at least one of the constituents used in the modified liquid medium ($A_1$) in the first stage.

That is, 0.5 g of wet callus obtained in the first stage was put into 30 ml of the medium ($B_1$, $B_2$, $B_3$ or $A_1$), and was cultured on a rotary shaker in the same manner as in the first stage.

After 14 days culture, the callus of *L. erythrorhizon* was separated by filtration, and dried for 24 hours at 35° C. and was weighed in dry state. Thus, the dry weight of cultured cells per 1 liter of the liquid medium ($B_1$, $B_2$, $B_3$ or $A_1$) was determined.

Shikonin was extracted from the obtained cells, and was weighed to determining the total shikonin production per 1 liter of the liquid medium ($B_1$, $B_2$, $B_3$ or $A_1$).

In the comparative examples as described herein, the second stage was conducted by using the same medium as in the first stage.

The results are shown in Table 2.

EXAMPLES 4 THROUGH 34 AND COMPARATIVE EXAMPLE 2

(Culture in the first stage)

Thirty mililiters of a modified Linsmaier-Skoog liquid medium ($A_2$) having a composition as shown in Table 3 (containing 1 μM of indoleacetic acid, 10 μM of kinetin, and 30 g/liter of sucrose) was put into a 100 ml Erlenmeyer flask and sterilized for 10 minutes at 120° C.

After being cooled, 0.5 g of fresh callus of *L. erythrorhizon* (obtained by culture on the agar medium) was added to the above medium ($A_2$), and was cultured at 25° C. for a period of 14 days on a rotary shaker at agitation diameter of 25 mm and speed of 100 rpm.

Using 0.5 g of the cells obtained by the above mentioned culture, the same operation was repeated (usually twice). As a result, the growth of cells in the modified liquid medium ($A_2$) was stabilized.

(Culture in the second stage)

The second stage was conducted by using the above medium ($A_2$) or a medium ($B_4$ through $B_{34}$) shown in Table 3 which was prepared by increasing or decreasing the concentration of at least one of the constituents used in the modified liquid medium ($A_2$) in the first stage.

That is, 0.5 g of wet callus obtained in the first stage was put into 30 ml of the medium ($B_4$ through $B_{34}$ or $A_2$), and was cultured on a rotary shaker in the same manner as in the first stage.

After 14 days culture, the callus of *L. erythrorhizon* was separated by filtration, and dried for 24 hours at 35° C. and was weighed in dry stage. Thus, the dry weight of cultured cells per 1 liter of the liquid medium ($B_4$ through $B_{34}$ or $A_2$) was determined.

Shikonin was extracted from the obtained callus, and was weighed to determine the total shikonin production per 1 liter of the liquid medium ($B_4$ through $B_{34}$ or $A_2$).

The results are shown in Table 4.

EXAMPLES 35 AND 36, AND COMPARATIVE EXAMPLES 3 AND 4

(Culture in the first stage)

Thirty mililiters of a modified Linsmaier-Skoog liquid medium ($A_3$ or $A_4$) having a composition as shown in Table 5 was put into a 100 ml Erlenmeyer flask, and sterilized for 10 minutes at 120° C.

After being cooled, 0.5 g of fresh callus of *Coptis japonica* or *Nicotiania tabacum* (obtained by culture on the agar medium) was added to the above medium ($A_3$ or $A_4$), and was cultured at 25° C. for a period of 14 days on a rotary shaker at agitation diameter of 25 mm and speed of 100 rpm.

Using 0.5 g of the cells obtained by above mentioned culture, the same operation was repeated (usually twice). As a result, the growth of cells in the modified liquid medium ($A_3$ or $A_4$) was stabilized.

(Culture in the second stage)

The second stage was conducted by using a medium ($B_{35}$ or $B_{36}$) shown in Table 5 which was prepared by increasing or decreasing the concentration of at least one of the constituents used in the modified liquid medium ($A_3$ or $A_4$) in the first stage.

That is, 0.5 g of wet callus obtained in the first stage was put into 30 ml of the medium ($B_{35}$ or $B_{36}$), and was cultured on a rotary shaker in the same manner as in the first stage.

After 14 days culture, the callus of *Coptis japonica* or Nicotinia tabacum was separated by filtration, and dried for 24 hours at 35° C. and was weighed in dry state. Thus, the dry weight of cultured cells per 1 liter of the liquid medium ($B_{35}$ or $B_{36}$) was determined.

Berberine or nicotine was extracted from the obtained callus, and was weighed to determine the total production of berberine or nicotine per 1 liter of the liquid medium ($B_{35}$ or $B_{36}$).

The results are shown in Table 6.

TABLE 1

| Class | Constituents | | $A_1$ | $B_1$ | $B_2$ | $B_3$ |
|---|---|---|---|---|---|---|
| Inorganic substances | $NH_4NO_3$ | (mM) | 21 | — | — | — |
| | $KNO_3$ | (mM) | 19 | 1.9 | 1.9 | 1.9 |
| | $CaCl_2.2H_2O$ | (mM) | 3.0 | 3.0 | 3.0 | 3.0 |
| | $MgSo_4.7H_2O$ | (mM) | 3.0 | 3.0 | 3.0 | 3.0 |
| | $KH_2PO_4$ | (mM) | 1.25 | 0.125 | 0.125 | 0.125 |

TABLE 1-continued

| Class | Constituents | | $A_1$ | $B_1$ | $B_2$ | $B_3$ |
|---|---|---|---|---|---|---|
| | KI | (μM) | 5 | 5 | — | — |
| | $H_3BO_3$ | (μM) | 100 | 100 | 100 | 100 |
| | $MnSO_4.4H_2O$ | (μM) | 100 | 100 | — | — |
| | $ZnSO_4.7H_2O$ | (μM) | 30 | 30 | 30 | 30 |
| | $Na_2MoO_4.2H_2O$ | (μM) | 1 | 1 | — | — |
| | $CuSO_4.5H_2O$ | (μM) | 0.6 | 0.6 | 0.6 | 0.6 |
| | $CoCl_2.6H_2O$ | (μM) | 0.1 | 0.1 | — | — |
| | $Na_3EDTA$ | (μM) | 100 | 100 | 10 | 10 |
| | $FeSO_4.7H_2O$ | (μM) | 100 | 100 | 10 | 10 |
| Carbon source | Sucrose | (g/l) | 30 | 30 | 30 | 30 |
| Vitamins | Inositol | (mg/l) | 100 | 100 | 100 | — |
| | Thiamine | (mg/l) | 0.4 | 0.4 | 0.4 | — |
| Amino acids | Glycine | (mg/l) | 0.2 | 0.2 | 0.2 | — |
| Phyto-hormones | IAA | (μM) | 1 | 1 | 1 | 1 |
| | Kinetin | (μM) | 10 | 10 | 10 | — |

(Note)
$Na_3EDTA$: trisodium salt of ethylenediaminetetraacetic acid
IAA: indoleacetic acid

TABLE 2

| Examples | Comp. Ex. 1 | Ex. 1 | Ex. 2 | Ex. 3 |
|---|---|---|---|---|
| first stage/ second stage Products | $A_1/A_1$ | $A_1/B_1$ | $A_1/B_2$ | $A_1/B_3$ |
| Callus (g/l) | 20.0 | 9.0 | 9.3 | 10.0 |
| Shikonin (mg/l) | <100 | 740 | 970 | 1300 |

TABLE 3

| Class | Constituents | $A_2$ | $B_4$ | $B_5$ | $B_6$ | $B_7$ | $B_8$ | $B_9$ | $B_{10}$ | $B_{11}$ | $B_{12}$ | $B_{13}$ | $B_{14}$ | $B_{15}$ | $B_{16}$ | $B_{17}$ | $B_{18}$ |
|---|---|---|---|---|---|---|---|---|---|---|---|---|---|---|---|---|---|
| Inorganic substances | $NH_4NO_3$ (mM) | 21 | 3.8 | 2.1 | 21 | 21 | 21 | 21 | 3.8 | 2.1 | 2.1 | 2.1 | 21 | 21 | 3.8 | 3.8 | 2.1 |
| | $KNO_3$ (mM) | 19 | 3.5 | 1.9 | 19 | 19 | 3.5 | 1.9 | 3.5 | 1.9 | 1.9 | 1.9 | 19 | 19 | 3.5 | 3.5 | 1.9 |
| | $NaNO_3$ (mM) | — | — | — | — | — | 15.3 | 16.9 | — | — | — | — | — | — | — | — | — |
| | $CaCl_2.2H_2O$ (mM) | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 |
| | $MgSO_4.7H_2O$ (mM) | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 |
| | $KH_2PO_4$ (mM) | 1.25 | 1.25 | 1.25 | 0.22 | 0.125 | 1.25 | 1.25 | 0.22 | 0.125 | 0.125 | 0.125 | 1.25 | 1.25 | 0.22 | 0.22 | 0.125 |
| | KI (μM) | 5 | 5 | 5 | 5 | 5 | 5 | 5 | 5 | 5 | 5 | 5 | 5 | 5 | 5 | 5 | 5 |
| | $H_3BO_3$ (μM) | 100 | 100 | 100 | 100 | 100 | 100 | 100 | 100 | 100 | 100 | 100 | 100 | 100 | 100 | 100 | 100 |
| | $MnSO_4.4H_2O$ (μM) | 100 | 100 | 100 | 100 | 100 | 100 | 100 | 100 | 100 | 100 | 100 | 100 | 100 | 100 | 100 | 100 |
| | $ZnSO_4.7H_2O$ (μM) | 30 | 30 | 30 | 30 | 30 | 30 | 30 | 30 | 30 | 30 | 30 | 30 | 30 | 30 | 30 | 30 |
| | $Na_2MoO_4.2H_2O$ (μM) | 1 | 1 | 1 | 1 | 1 | 1 | 1 | 1 | 1 | 1 | 1 | 1 | 1 | 1 | 1 | 1 |
| | $CuSO_4.5H_2O$ (μM) | 0.1 | 0.1 | 0.1 | 0.1 | 0.1 | 0.1 | 0.1 | 0.1 | 0.1 | 0.3 | 1.2 | 0.3 | 1.2 | 0.3 | 1.2 | 2.4 |
| | $CoCl_2.6H_2O$ (μM) | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| | $Na_3EDTA$ (μM) | 100 | 100 | 100 | 100 | 100 | 100 | 100 | 100 | 100 | 100 | 100 | 100 | 100 | 100 | 100 | 100 |
| | $FeSO_4.7H_2O$ (μM) | 100 | 100 | 100 | 100 | 100 | 100 | 100 | 100 | 100 | 100 | 100 | 100 | 100 | 100 | 100 | 100 |
| | KCl (mM) | — | 15.3 | 16.9 | — | — | — | — | — | — | — | — | — | — | — | — | — |
| Carbon source | Sucrose (g/l) | 30 | 30 | 30 | 30 | 30 | 30 | 30 | 30 | 30 | 30 | 30 | 30 | 30 | 30 | 30 | 30 |
| Vitamins | Inositol (mg/l) | 100 | 100 | 100 | 100 | 100 | 100 | 100 | 100 | 100 | 100 | 100 | 100 | 100 | 100 | 100 | 100 |
| | Thiamine (mg/l) | 0.4 | 0.4 | 0.4 | 0.4 | 0.4 | 0.4 | 0.4 | 0.4 | 0.4 | 0.4 | 0.4 | 0.4 | 0.4 | 0.4 | 0.4 | 0.4 |
| Amino acids | Glycine (mg/l) | 2 | 2 | 2 | 2 | 2 | 2 | 2 | 2 | 2 | 2 | 2 | 2 | 2 | 2 | 2 | 2 |
| | L-glutamine (mg/l) | 2 | 2 | 2 | 2 | 2 | 2 | 2 | 2 | 2 | 2 | 2 | 2 | 2 | 2 | 2 | 2 |
| Phyto-hormones | IAA (μm) | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| | Kinetin (μM) | 10 | 10 | 10 | 10 | 10 | 10 | 10 | 10 | 10 | 10 | 10 | 10 | 10 | 10 | 10 | 10 |

| Class | Constituents | $B_{19}$ | $B_{20}$ | $B_{21}$ | $B_{22}$ | $B_{23}$ | $B_{24}$ | $B_{25}$ | $B_{26}$ | $B_{27}$ | $B_{28}$ | $B_{29}$ | $B_{30}$ | $B_{31}$ | $B_{32}$ | $B_{33}$ | $B_{34}$ |
|---|---|---|---|---|---|---|---|---|---|---|---|---|---|---|---|---|---|
| Inorganic substances | $NH_4NO_3$ (mM) | 2.1 | 2.1 | 2.1 | 2.1 | 2.1 | 2.1 | 2.1 | 2.1 | 2.1 | 2.1 | 2.1 | 2.1 | 2.1 | 2.1 | 2.1 | 2.1 |
| | $KNO_3$ (mM) | 1.9 | 1.9 | 1.9 | 1.9 | 1.9 | 1.9 | 1.9 | 1.9 | 1.9 | 1.9 | 1.9 | 1.9 | 1.9 | 1.9 | 1.9 | 1.9 |
| | $NaNO_3$ (mM) | — | — | — | — | — | — | — | — | — | — | — | — | — | — | — | — |
| | $CaCl_2.2H_2O$ (mM) | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 |
| | $MgSO_4.7H_2O$ (mM) | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 |
| | $KH_2PO_4$ (mM) | 0.125 | 0.125 | 0.125 | 0.125 | 0.125 | 0.125 | 0.125 | 0.125 | 0.125 | 0.125 | 0.125 | 0.125 | 0.125 | 0.125 | 0.125 | 0.125 |
| | KI (μM) | 5 | 5 | 0.5 | — | 5 | 5 | 5 | — | 5 | 5 | 5 | 5 | 5 | 5 | 0.08 | — |
| | $H_3BO_3$ (μM) | 100 | 100 | 100 | 100 | 100 | 100 | 100 | 100 | 100 | 100 | 100 | 100 | 100 | 100 | 100 | 100 |
| | $MnSO_4.4H_2O$ (μM) | 9.0 | — | 100 | 100 | 100 | 100 | 9 | — | 100 | 100 | 100 | 100 | 100 | 100 | 2.0 | — |
| | $ZnSO_4.7H_2O$ (μM) | 30 | 30 | 30 | 30 | 30 | 30 | 30 | 30 | 30 | 30 | 30 | 30 | 30 | 30 | 30 | 30 |
| | $Na_2MoO_4.2H_2O$ (μM) | 1 | 1 | 1 | 1 | 0.08 | — | 0.08 | — | 1 | 1 | 1 | 1 | 1 | 1 | 0.02 | — |
| | $CuSO_4.5H_2O$ (μM) | 1.2 | 1.2 | 1.2 | 1.2 | 1.2 | 1.2 | 1.2 | 1.2 | 1.2 | 1.2 | 1.2 | 1.2 | 1.2 | 1.2 | 0.08 | 0.3 |
| | $CoCl_2.6H_2O$ (μM) | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| | $Na_3EDTA$ (μM) | 100 | 100 | 100 | 100 | 100 | 100 | 100 | 100 | 100 | 100 | 100 | 100 | 100 | 100 | 100 | 100 |
| | $FeSO_4.7H_2O$ (μM) | 100 | 100 | 100 | 100 | 100 | 100 | 100 | 100 | 100 | 100 | 100 | 100 | 100 | 100 | 100 | 100 |

TABLE 3-continued

| | | | | | | | | | | | | | | | | | |
|---|---|---|---|---|---|---|---|---|---|---|---|---|---|---|---|---|---|
| | KCl (mM) | — | — | — | — | — | — | — | — | — | — | — | — | — | — | — | — |
| Carbon source | Sucrose (g/l) | 30 | 30 | 30 | 30 | 30 | 30 | 30 | 30 | 30 | 30 | 30 | 30 | 30 | 30 | 30 | 30 |
| Vitamins | Inositol (mg/l) | 100 | 100 | 100 | 100 | 100 | 100 | 100 | 100 | 8 | — | 100 | 100 | 100 | 100 | 8 | — |
| | Thiamine (mg/l) | 0.4 | 0.4 | 0.4 | 0.4 | 0.4 | 0.4 | 0.4 | 0.4 | 0.03 | — | 0.4 | 0.4 | 0.4 | 0.4 | 0.03 | — |
| Amino acids (mg/l) | Glycine (mg/l) | 2 | 2 | 2 | 2 | 2 | 2 | 2 | 2 | 2 | 2 | 0.01 | — | 2 | 2 | 0.01 | — |
| | L-glutamine | 2 | 2 | 2 | 2 | 2 | 2 | 2 | 2 | 2 | 2 | 0.01 | — | 2 | 2 | 0.01 | — |
| Phyto-hormones | IAA ($\mu$M) | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| | Kinetin ($\mu$M) | 10 | 10 | 10 | 10 | 10 | 10 | 10 | 10 | 10 | 10 | 10 | 10 | 0.1 | — | 0.1 | — |

TABLE 4

| Examples | Comp. Ex. 2 | Ex. 4 | Ex. 5 | Ex. 6 | Ex. 7 | Ex. 8 | Ex. 9 | Ex. 10 | Ex. 11 | Ex. 12 | Ex. 13 |
|---|---|---|---|---|---|---|---|---|---|---|---|
| First stage/Second stage Products | $A_2/A_2$ | $A_2/B_4$ | $A_2/B_5$ | $A_2/B_6$ | $A_2/B_7$ | $A_2/B_8$ | $A_2/B_9$ | $A_2/B_{10}$ | $A_2/B_{11}$ | $A_2/B_{12}$ | $A_2/B_{13}$ |
| Callus (g/l) | 20.0 | 19.0 | 14.2 | 16.5 | 7.7 | 18.1 | 17.0 | 12.2 | 8.3 | 8.5 | 8.6 |
| Shikonin (mg/l) | <100 | 110 | 200 | 280 | 400 | 130 | 150 | 420 | 500 | 690 | 850 |

| Examples | Ex. 14 | Ex. 15 | Ex. 16 | Ex. 17 | Ex. 18 | Ex. 19 | Ex. 20 | Ex. 21 | Ex. 22 | Ex. 23 | Ex. 24 |
|---|---|---|---|---|---|---|---|---|---|---|---|
| First stage/Second stage Products | $A_2/B_{14}$ | $A_2/B_{15}$ | $A_2/B_{16}$ | $A_2/B_{17}$ | $A_2/B_{18}$ | $A_2/B_{19}$ | $A_2/B_{20}$ | $A_2/B_{21}$ | $A_2/B_{22}$ | $A_2/B_{23}$ | $A_2/B_{24}$ |
| Callus (g/l) | 20.4 | 20.6 | 12.4 | 13.1 | 8.3 | 8.7 | 8.7 | 8.5 | 8.8 | 8.3 | 8.3 |
| Shikonin (mg/l) | 150 | 200 | 480 | 550 | 850 | 530 | 550 | 540 | 570 | 530 | 530 |

| Example | Ex. 25 | Ex. 26 | Ex. 27 | Ex. 28 | Ex. 29 | Ex. 30 | Ex. 31 | Ex. 32 | Ex. 33 | Ex. 34 |
|---|---|---|---|---|---|---|---|---|---|---|
| First stage/Second stage Products | $A_2/B_{25}$ | $A_2/B_{26}$ | $A_2/B_{27}$ | $A_2/B_{28}$ | $A_2/B_{29}$ | $A_2/B_{30}$ | $A_2/B_{31}$ | $A_2/B_{32}$ | $A_2/B_{33}$ | $A_2/B_{34}$ |
| Callus (g/l) | 8.9 | 9.1 | 9.2 | 9.5 | 9.0 | 9.2 | 9.0 | 9.2 | 9.9 | 10.0 |
| Shikonin (mg/l) | 570 | 640 | 620 | 700 | 580 | 590 | 690 | 700 | 1010 | 1300 |

TABLE 5

| Class | Constituents | | Coptis $A_3$ | Coptis $B_{35}$ | Nicotiana $A_4$ | Nicotiana $B_{36}$ |
|---|---|---|---|---|---|---|
| Inorganic substances | $NH_4NO_3$ | (mM) | 18 | 2.1 | 18 | 2.1 |
| | $KNO_3$ | (mM) | 19 | 1.9 | 19 | 1.9 |
| | $CaCl_2.2H_2O$ | (mM) | 1.1 | 3.0 | 1.1 | 3.0 |
| | $MgSO_4.7H_2O$ | (mM) | 0.75 | 3.0 | 0.75 | 3.0 |
| | $KH_2PO_4$ | (mM) | 1.0 | 0.125 | 1.0 | 0.125 |
| | KI | ($\mu$M) | 5 | — | 5 | — |
| | $H_3BO_3$ | ($\mu$M) | 161 | 100 | 161 | 100 |
| | $MnSO_4.4H_2O$ | ($\mu$M) | 112 | — | 112 | — |
| | $ZnSO_4.7H_2O$ | ($\mu$M) | 35 | 30 | 35 | 30 |
| | $Na_2MoO_4.2H_2O$ | ($\mu$M) | 1 | — | 1 | — |
| | $CuSO_4.5H_2O$ | ($\mu$M) | 0.1 | 0.3 | 0.1 | 0.3 |
| | $Na_3EDTA$ | ($\mu$M) | 100 | 100 | 100 | 100 |
| | $FeSO_4.7H_2O$ | ($\mu$M) | 100 | 100 | 100 | 100 |
| Carbon source | Sucrose | (g/l) | 20 | 30 | 20 | 30 |
| Vitamins | Inositol | (mg/l) | 100 | — | 100 | — |
| | Thiamine | (mg/l) | 0.5 | — | 0.5 | — |
| Amino acids | Glycine | (mg/l) | 2 | — | 2 | — |
| Phyto-hormones | IAA | ($\mu$M) | — | 1.0 | 10 | 1.0 |
| | Kinetin | ($\mu$M) | — | — | 1 | — |
| | NAA | ($\mu$M) | 10 | — | — | — |
| | BA | ($\mu$M) | 0.007 | — | — | — |

TABLE 6

| Examples | Comp. EX. 3 | Ex. 35 | Comp. Ex. 4 | Ex. 36 |
|---|---|---|---|---|
| First stage/Second stage | $A_3/A_3$ | $A_3/B_{35}$ | $A_4/A_4$ | $A_4/B_{36}$ |
| Callus (g/l) | 10.0 | 7.5 | 13.2 | 1.4 |
| Products (mg/l) | berberine 170 | berberine 300 | nicotine 1.4 | nicotine 2.3 |

What is claimed is:

1. A method for producing secondary metabolites of Juglandaceae plants, Boraginaceae plants, Pyrolaceae plants, Plumbaginaceae plants, Lythraceae plants, or Ranunculaceae plants, by culturing cells of said plants obtained by culturing in a first liquid medium, the composition thereof favoring the growth of said plants and comprising inorganic substances and carbon sources as the essential constituents and further containing at least one of the group consisting of phytohormones, vitamins, and amino acids, and further culturing said cells obtained from the first medium in a second liquid medium, the composition of said second liquid medium favoring the production of the secondary metabolites, wherein the composition of the second liquid medium differs from the composition of the corresponding first liquid medium in at least two of the following concentrations (a) to (c), namely:

(a) the first medium contains inorganic nitrogen in an amount of 40 to 130 mM and the second medium contains inorganic nitrogen in a concentration of not more than 1/5 of the respective concentration in the first medium;

(b) the first medium contains inorganic phosphorus in an amount of 0.8 to 2.4 mM and the second medium contains inorganic phosphorus in a concentration of not more than 1/5 of the respective concentration in the first medium;

(c) the first medium contains potassium in an amount of 10 to 45 mM and the second medium contains potassium in a concentration of not more than 1/5 of the respective concentration in the first medium;

and concurrently in at least one of the concentrations (d) to (i), namely;

(d) the first medium contains copper ions in an amount of 0.015 to 0.15 $\mu$M, and the second medium contains copper ions in at least the three times concentration of the respective concentration in the first medium;

(e) the first medium contains manganese ions in an amount of 30 to 300 μM, iodine in an amount of 1 to 15 μM, and molybdate ions in an amount of 0.05 to 0.5 μM, and the second medium contains at least one of manganese ions, iodine ions, and molybdenum ions in a concentration of not more than 1/10 of the respective concentration in the first medium;

(f) the first medium contains vitamins in a total amount of 1 to 500 mg/liter, and the second medium contains vitamins in a concentration of not more than 1/10 of the respective concentration in the first medium;

(g) the first medium contains amino acids in a total amount of 0.1 to 100 mg/liter, and the second medium contains amino acids in a concentration of not more than 1/100 of the respective concentration in the first medium;

(h) the first medium contains cytokinins in a total amount of 0.01 to 10 μM and the second medium contains cytokinins in a concentration of not more than 1/100 of the respective concentration in the first medium;

(i) the first medium contains sulfate ions in an amount of 0.5 to 3 mM, and the second medium contains sulfate ions in at least the ten time concentration of the respective concentration in the first medium.

2. The method according to claim 1 wherein naphthoquinone derivatives are produced from plants of the Boraginacae family, Juglandacea family, or Lythraceae family.

3. The method according to claim 2 wherein the naphthoquinone derivative is Shikonin and the plant is *Lithospermum erythrorhizon*.

4. The method according to claim 1 wherein isoquinoline alkaloids are produced from plants of the Ranunculaceae family.

5. The method according to claim 4 wherein the isoquinoline alkaloid is berberine and the plant is *Coptis japonica*.

6. The method according to claim 1 wherein the composition of the second liquid medium differs from the composition of corresponding first liquid medium in all of the concentrations (a) to (c) and concurrently in *at least one* of the concentrations (d) to (i).

7. A method for producing secondary metabolites of Juglandaceae plants, Boraginaceae plants, Pyrolaceae plants, Plumbaginaceae plants, Lythraceae plants, or Ranunculaceae plants, by culturing cells of said plants obtained by culturing in a first liquid medium, the composition thereof favoring the growth of said plants and comprising inorganic substances and carbon sources as the essential constituents and further containing at least one of the group consisting of phytohormones, vitamins, and amino acids, and further culturing said cells obtained from the first medium in a second liquid medium, the composition of said second liquid medium favoring the production of the secondary metabolites, wherein the composition of the second liquid medium differs from the composition of the corresponding first liquid medium in all three of the following concentrations (a) to (c), namely:

(a) the first medium contains inorganic nitrogen in an amount of 40 to 130 mM and the second medium contains inorganic nitrogen in a concentration of not more than 1/5 of the respective concentration in the first medium;

(b) the first medium contains inorganic phosphorus in an amount of 0.8 to 2.4 mM and the second medium contains inorganic phosphorus in a concentration of not more than 1/5 of the respective concentration in the first medium;

(c) the first medium contains potassium in an amount of 10 to 45 mM and the second medium contains potassium in a concentration of not more than 1/5 of the respective concentration in the first medium.

8. The method according to claim 7 wherein naphthoquinone derivatives are produced from plants of the Boraginaceae family, Juglandacea family, or Lythraceae family.

9. The method according to claim 7 wherein isoquinoline alkaloids are produced from plants of the Ranunculaceae family.

* * * * *